United States Patent [19]

Thomas

[11] 4,026,282
[45] May 31, 1977

[54] PATIENT RESTRAINING GOWN

[76] Inventor: Lois Thomas, 1160 Chemawa Road NE., Salem, Oreg. 97303

[22] Filed: Oct. 20, 1975

[21] Appl. No.: 623,722

[52] U.S. Cl. .............................................. 128/134
[51] Int. Cl.² ........................................ A61F 13/00
[58] Field of Search ................... 128/133, 134, 135; 5/336; 297/384, 385

[56] References Cited

UNITED STATES PATENTS

| | | | |
|---|---|---|---|
| 2,044,390 | 6/1936 | Kiehs | 128/134 |
| 2,940,443 | 6/1960 | Baker | 297/384 X |
| 3,182,338 | 5/1965 | Shirrod | 5/336 |
| 3,265,065 | 8/1966 | Jillson | 128/134 |
| 3,680,554 | 8/1972 | Sanchez | 128/134 |
| 3,788,309 | 1/1974 | Zeilman | 128/134 |

Primary Examiner—Lawrence W. Trapp
Attorney, Agent, or Firm—Klarquist, Sparkman, Campbell, Leigh, Hall & Whinston

[57] ABSTRACT

A gown closed in front and open in the back has a wide belt secured to the inner, front portion of the gown. The belt passes through slits in the side portions of the gown, and one end portion of the belt is slidable in a longitudinal slit in the other end portion so that the patient can roll from side to side without restraint, the ends of the belt being secured to opposite sides of a bed or chair.

6 Claims, 5 Drawing Figures

U.S. Patent  May 31, 1977  4,026,282
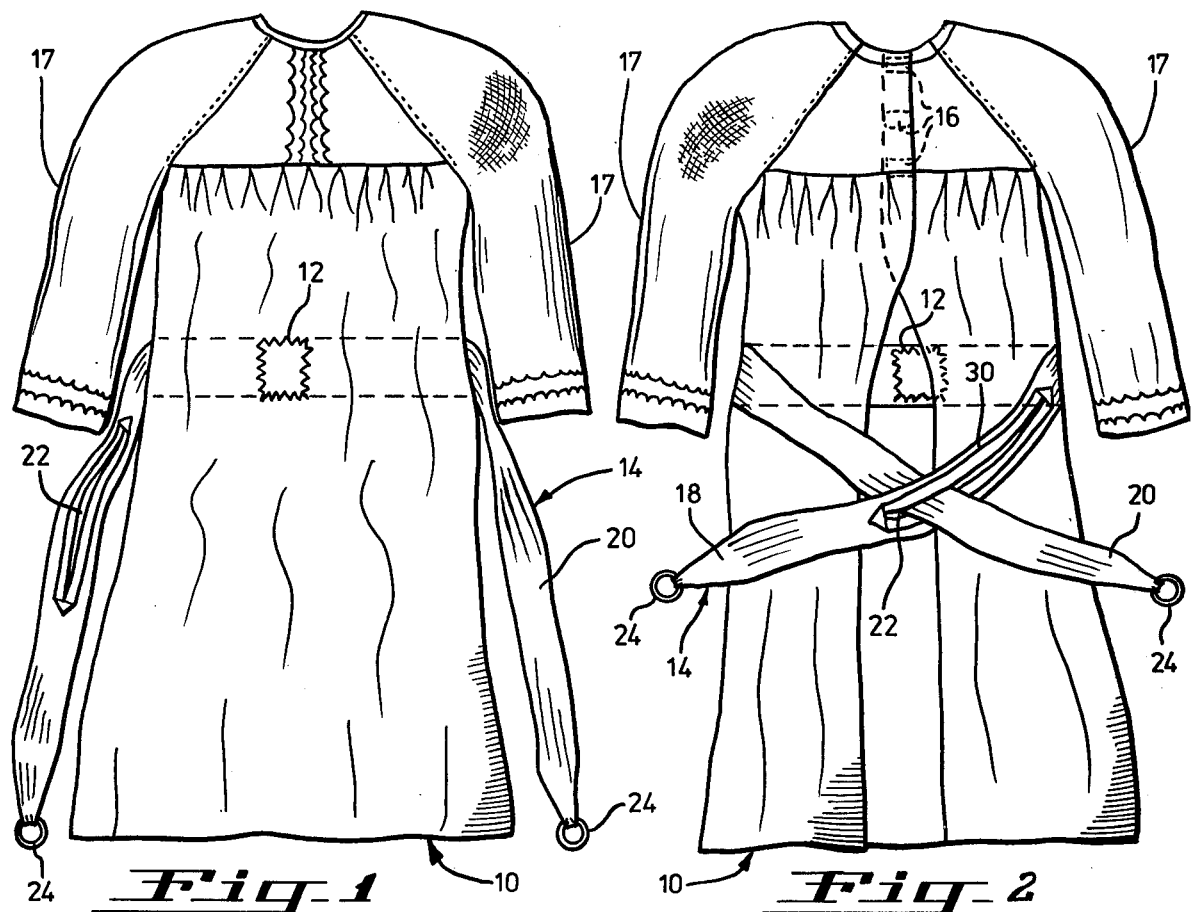
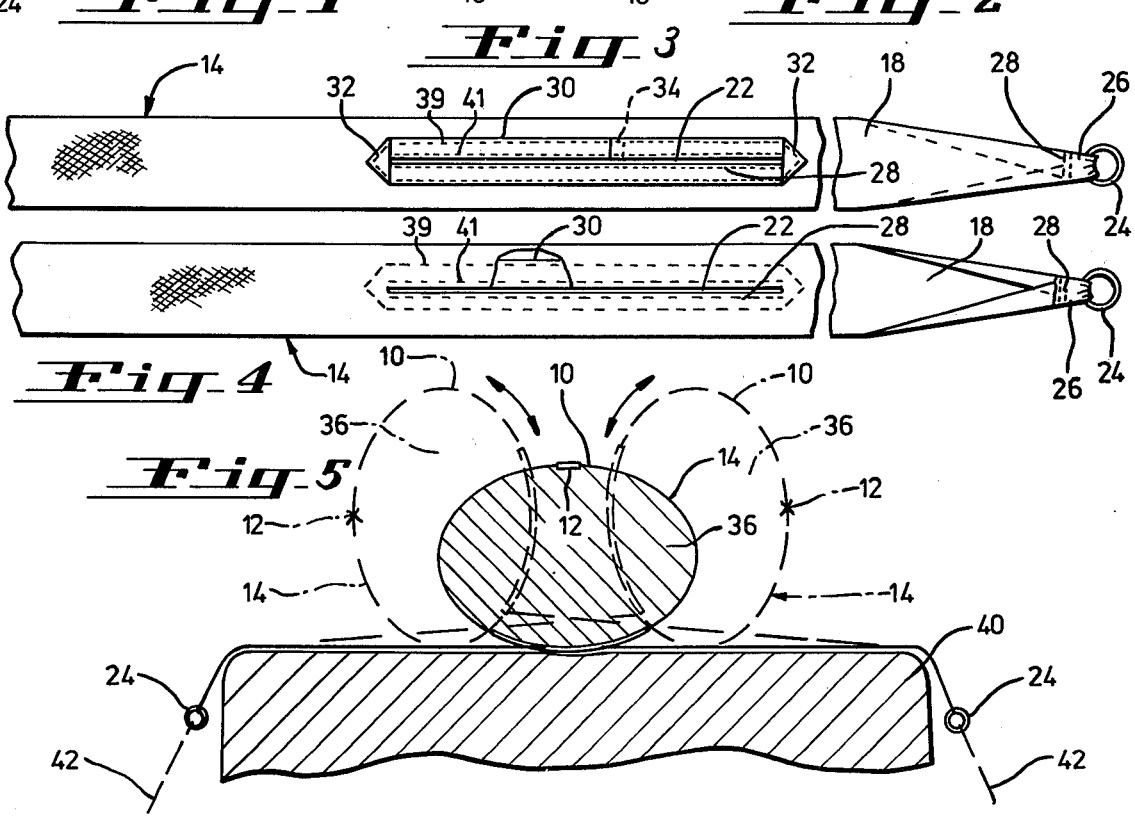

PATIENT RESTRAINING GOWN

DESCRIPTION

This invention relates to a patient restraining gown, and has for an object thereof the provision of a new and improved patient restraining gown.

Another object of the invention is to provide a patient restraining gown which permits a patient to turn freely from side to side.

A further object of the invention is to provide a patient restraining gown in which a belt attached to a gown has one end portion extending through a long slit in the other end portion to permit a patient wearing the gown to turn through a half circle.

In the drawings:

FIG. 1 is a front elevation view of a patient restraining gown forming one embodiment of the invention;

FIG. 2 is a rear elevation view of the gown of FIG. 1;

FIG. 3 is an enlarged, fragmentary face view of one end portion of a belt forming a portion of the gown of FIG. 1;

FIG. 4 is an enlarged, fragmentary face view of the other end portion of the belt of FIG. 3; and, FIG. 5 is a schematic, vertical sectional view of a bed with a patient wearing the gown thereon.

Referring now in detail to the drawings, there is shown therein a patient restraining gown forming one specific embodiment of the invention and including a gown 10 to the inside front portion of which is secured by stitching 12 the central portion of a restraining belt 14. The gown is closed at the front and open or slit at its back, preferably with one or more fasteners 16 such as, for example, Velcro fasteners, at its upper portion. The gown also has arms 17. End portions 18 and 20 of the belt extend through slits in the sides of the gown and the end portion 20 is passed through a long, longitudinally extending slit 22 in the end portion 18. Rings 24 are secured to the ends of the belt by folded in and folded back portions 26 secured in a loop by stitching 28.

The belt 14 is a strong web, preferably of sail cloth, and a binding 30 for the slit may be made of the same material. Each side of the sash is hemmed, and the binding strip is folded at each side to meet in the center and make a double thickness and is sewed along the center to make a long strip which is then folded at two portions 32 and is overlapped at 34. The binding is sewed onto the belt starting at a point that the slit 22 is substantially centered on the back of a patient 36 when the belt is somewhat loosely snugged up. I use a zig-zag stitch 41, like a bottom hole stitch, and sew down one inside edge of the binding, then come back up the other inside edge, then cut a slot like a bottom hole, and then go around it a second time with a zig-zag stitch. An outer stitch 39 also is made.

In FIG. 5, the patient 36 is shown loosely restrained on a bed 40 with the gown 10 on and cords 42 secured to the eyes 24. In the full line position, the patient is on her back, and the portion 20 of the belt passes through the slit 22 at substantially the center of the slit. The patient can then freely turn either onto her left side or her right side, as illustrated by the broken line positions, the end portion 20 sliding to either end of the slit 22 when the patient so turns so that there is no uncomfortable binding action. Viewed from the front, the belt is completely concealed, which is reassuring to many patients.

While the restraining gown is shown, as in FIG. 5, in use with the bed, the gown is equally efficacious in holding the patient on a chair.

What is claimed is:

1. In a restraining gown,
   a decorative gown portion having a front portion,
   a belt attached at its central portion to the front portion of the gown portion and confined to the sides of the gown portion,
   means securing the end portions of the belt together in crossed-over positions and permitting sliding movement between the end portions at least sufficiently for a patient to turn without restraint from a position on her back to a position on her side, the securing means being a long, reinforced, longitudinal slit in one of the end portions through which the other end portion extends and can move laterally,
   and a pair of connector means one on each end of the belt for securing the ends of the belt to sides of a bed or chair.

2. The restraining gown of claim 1 wherein the belt is of woven fabric.

3. The restraining gown of claim 1 wherein the connector means are rings.

4. The restraining gown of claim 1, wherein the slit is sufficiently long to permit turning about 180°.

5. The restraining gown of claim 4 wherein the central portion of the belt is located inside the front portion of the gown and the gown has slits in the sides thereof through which the end portions of the belt extend from the inside of the gown to the outside thereof.

6. The restraining gown of claim 1 wherein the central portion of the gown is located at the inside face of the gown, and the gown has openings in the sides thereof through which the belt extends.

* * * * *